United States Patent [19]
Trimbo et al.

[11] Patent Number: 5,728,678
[45] Date of Patent: Mar. 17, 1998

[54] METHOD AND COMPOSITION FOR PROVIDING NUTRITION TO A RENAL FAILURE PATIENT

[75] Inventors: Susan Trimbo, Evanston; Diana Twyman, Chicago; David Madsen, Libertyville; Shen-Youn Chang, Wadsworth; Hugh N. Tucker, Barrington, all of Ill.

[73] Assignee: Nestec Ltd., Vevey, Switzerland

[21] Appl. No.: 470,985

[22] Filed: Jun. 6, 1995

[51] Int. Cl.$^6$ .............................. A61K 38/00; A23J 1/00
[52] U.S. Cl. .................. 514/12; 514/2; 514/561; 514/869; 514/943; 426/583; 426/656; 426/657; 424/535
[58] Field of Search ..................... 514/12, 2, 561, 514/869, 943; 426/583, 656, 657; 424/535

[56] References Cited

U.S. PATENT DOCUMENTS

| | | | |
|---|---|---|---|
| 4,357,343 | 11/1982 | Madsen et al. | 424/274 |
| 4,678,807 | 7/1987 | Cotter et al. | 514/552 |
| 4,898,879 | 2/1990 | Madsen et al. | 514/400 |
| 4,920,098 | 4/1990 | Cotter et al. | 514/2 |
| 5,093,143 | 3/1992 | Behr et al. | 426/583 |
| 5,294,642 | 3/1994 | Ashauazi et al. | 514/561 |
| 5,378,722 | 1/1995 | Madsen et al. | 514/410 |
| 5,571,783 | 11/1996 | Montagne et al. | 514/2 |
| 5,576,287 | 11/1996 | Zaloga et al. | 514/2 |

FOREIGN PATENT DOCUMENTS

| | | |
|---|---|---|
| 0 442 140 A1 | 8/1991 | European Pat. Off. |
| 1 306 402 | 2/1973 | United Kingdom. |
| WO 85/03863 | 9/1985 | WIPO. |

OTHER PUBLICATIONS

F. Manz, et al., *Special Cow's Milk Formula and Special Whey Protein Concentrate with Low Phosphorus Content for Dietary Treatment in Renal Failure*, Akt. Ernähr.-Med., vol. 18, pp. 38–40 (1993).
Abbott et al, *Treatment of Acute Renal Insufficiency After Aortoiliac Surgery*, Arch Surg, vol. 103, pp. 590–594 (1971).
Alverstrand et al, *Clinical experience with amino acid and keto acid diets*, the American Journal of Clinical Nutrition, vol. 33, pp. 1654–1659 (1980).
Bergström et al, *Intracellular free amino acids in uremic patients as influenced by amino acid supply*, Kidney International, vol. 7, pp. S-345–S-348 (1975).
Breach, *Protein and Calorie Requirements in Acute Renal Failure*, American Dietetic Association, pp. 5, 12, 14 (1989).
Clinical Nutrition Cases, *Fat-Soluble Vitamin Nutrition in Patients with Chronic Renal Disease*, Nutrition Reviews, vol. 39, No. 5, pp. 212–214 (1981).
Clintec Nutrition Company Brochure, *Travasorb® Renal* (1981).
Clintec Nutrition Company Brochure, *RenAmin® (Amino Acid) Injection* (1988).
Feinstein, *Parenteral Nutrition in Acute Renal Failure*, Am. J. Nephrol., vol. 5, pp. 145–149 (1985).

Feinstein et al, *Nutrition Therapy in Acute Renal Failure*, Nutrition and the Kidney, Little Brown and Company, Mitch et al, Eds., Chapter 4, pp. 80–103.
Fürst et al, *Principles of essential amino acid therapy in uremia*, The American Journal of Clinical Nutrition, vol. 31, pp. 1744–1755 (1978).
Giacchino et al, *Surgery, Nutritional Support, and Survival in Patients With End-Stage Renal Disease*, Arch Surg, vol. 116, pp. 634–640 (1981).
Giordano et al, *Nitrogen balance in uremic patients on different amino acid and keto acid formulations–a proposed reference pattern*, The American Journal of Clinical Nutrition, vol. 31, pp. 1797–1801 (1978).
Hunsicker, *Nutritional Requirements of Renal Transplant Patients*, Chapter 10, pp. 224–238.
Hutchins et al, *Iron and Folate Metabolism in Renal Failure*, Seminars in Nephrology, vol. 5, No. 2, pp. 142–146 (1985).
Kendall McGaw Laboratories, Inc., *Amin-Acid® Instant Drink*, Nutrition and Usage Information (1988).
Kopple, *Dietary Considerations in Patients With Advanced Chronic Renal Failure, Acute Renal Failure, and Transplantation*, Diseases of the Kidney, Schrierer et al, Eds., p. 3417 (1987).
Kopple et al, *Evidence that Histidine is an Essential Amino Acid in Normal and Chronically Uremic Man*, The Journal of Clinical Investigation, vol. 55, pp. 881–891 (1975).
Marumo et al, *Deranged concentrations of water-soluble vitamins in the blood of undialyzed and dialyzed patients with chronic renal failure*, The International Journal of Artificial Organs, vol. 9, No. 1, pp. 17–24 (1986).
Oken, *Hemodyamic Basis for Human Acute Renal Failure (Vasomotor Nephropathy)*, The American Journal of Medicine, vol. 76, pp. 702–710 (1984).
Piraino et al, *Prolonged Hyperalimentation in Catabolic Chronic Dialysis Therapy Patients*, Journal of Parenteral and Enteral Nutrition, vol. 5, No. 6, pp. 463–477 (1981).
Powers, *Prolonged Experience with Intradialytic Hyperalimentation in Marasmic Chronic Hemodialysis Patients*, Contemporary Dialysis & Nephrology, pp. 22–29 (1989).
Powers et al, *Prolonged Intradialysis Hyperalimentation in Chronic Hemodialysis Patients with an Amino Acid Solution (RenAmin® (Amino Acid) Injunction) Formulated for Renal Failure*, Perspectives in Clinical Nutrition, Chapter 14, pp. 191–202 (1989).
Rainford, *Nutritional Management of Acute Renal Failure*, Acta Chir. Scand. Suppl., No. 507, pp. 327–329 (1981).
Ross Laboratories Brochure, *Specialized Nutrition for Patients With Renal Disease*, pp. 1–53 (1990).

(List continued on next page.)

*Primary Examiner*—Cecilia J. Tsang
*Assistant Examiner*—Abdel A. Mohamed
*Attorney, Agent, or Firm*—Hill, Steadman & Simpson

[57] ABSTRACT

The present invention provides a composition as well as method for providing nutrition to renal patients. Pursuant to the present invention, the enteral composition includes an effective amount of a protein source including whey protein and free amino acids that provide essential as well as nonessential amino acids. The composition is calorically dense and has a moderate osmolality.

23 Claims, No Drawings

OTHER PUBLICATIONS

Rudman et al, *Nutritional Requirements of Normal Adults*, Chapter 1, pp. 1–28.

Said et al, *Intestinal Absorption of 5-methyltetrahydrofolate in Experimental Uremia*, ACTA Vitaminol. Enzymol., vol 6(4), pp. 339–346 (1984).

Stein et al, *Vitamin Levels in Chronic Renal Failure and Need for Supplementation*, Blood Purification, vol. 3, pp. 52–62 (1985).

Wolfson et al, *Effect of Vitamin B–6 Deficiency on Plasma Amino Acid Levels in Chronically Azotemic Rats*, J. Nutr., vol. 116, pp. 1865–1872 (1986).

METHOD AND COMPOSITION FOR PROVIDING NUTRITION TO A RENAL FAILURE PATIENT

BACKGROUND OF THE INVENTION

The present invention relates to nutritional compositions for the support and therapy of individuals. More specifically, the present invention relates to nutritional compositions and methods of using same for preventing or treating renal failure.

Renal failure may be classified as acute or chronic. An abrupt, often reversible impairment (partial or total) of renal function, manifested by inadequate urine formation characterizes acute renal failure (ARF). ARF refers to the clinical conditions associated with rapid, steadily increasing azotemia, with or without oliguria (<500 mL/day). The causes of ARF can be grouped into three diagnostic categories: pre-renal (inadequate renal perfusion); post-renal (obstruction); and renal. *Merck Manual*, 16th Edition, p. 1661 (1992).

Patients with ARF very often are subject to such complications as sepsis and hypercatabolism. Using dialysis, the fluid and electrolyte abnormalities of ARF can be regulated, and uremic symptoms reduced. However, dialysis cannot alone prevent the ravages of catabolism, including poor wound healing, the risk of infections and increased mortality. Nutritional support must be used to maintain nutritional status until the ARF improves. *Handbook of Clinical Nutrition*, 2nd Edition, p. 336 (1989).

In contrast with ARF, chronic renal failure (CRF) refers to the clinical condition resulting from a multitude of pathologic processes that lead to derangement and insufficiency of renal excretory and regulatory function (uremia). CRF may result from any cause of renal dysfunction of sufficient magnitude. The functional effects of CRF can be grouped into three states: diminished renal reserve, renal insufficiency (failure) and uremia. *Merck Manual*, 16th Edition, p. 1665 (1992).

A gradual destruction of a number of functional nephrons and thus gradual reduction of renal functional capacity characterizes CRF. Progressive CRF produces wasting of both lean and fat body mass, reduced growth rates in children, and diminished synthesis of proteins including albumin. By careful dietary management, especially of protein intake, the progression of CRF may often times be stabilized and dialysis avoided. *Handbook of Clinical Nutrition*, 2nd Edition, p. 336 (1989).

As an alternate or in conjunction with dialysis, supplying amino acids alone or as dietary supplements has been utilized to support renal failure. While a variety of amino acid mixtures have been utilized, the inventors believe such heretofore employed compositions fail to meet all the necessary nutritional needs of the patient. For example, patients suffering from ARF experience increased energy needs that at times may be increased by as much as 35%. However, at the same time, fluid restriction is critical when treating renal patients.

As a result, patients suffering from renal failure require a high caloric intake with minimal water intake. Inadequate caloric intake contributes to increased protein breakdown and accelerated urea formation. Still further, patients who develop ARF from nephrotoxic drugs or radio-contrast agents require a diet with adequate calories as well as a restricted quantity of high biological value protein. The inventors believe the currently employed formulas fail to adequately meet all these necessary needs of the renal patient with a suitable product formulation.

Therefore, a need exists for a new composition for preventing and treating renal failure that supplies sufficient energy with restricted water intake.

SUMMARY OF THE INVENTION

The present invention provides a nutritional composition as well as methods of using same for treating patients suffering from or at risk of renal failure. To this end, the present invention uniquely provides an amino acid based, liquid ready-to-use product with a high caloric density and a moderate osmolality for renal patients. The high caloric density of the product provides patients sufficient energy without high intakes of water. In addition, the moderate osmolality of the product promotes easy tolerance for patients.

The present invention provides an improved nutritional composition for treating renal failure. The nutritional composition includes a therapeutically effective amount of a protein source including free amino acids and whey protein. The amino acid profile of the resulting protein source includes L-valine, L-leucine, L-isoleucine, L-threonine, L-methionine, L-lysine, L-phenylalanine, L-tryptophan, L-histidine, L-arginine, L-proline, glycine, L-alanine, L-serine, L-tyrosine, L-cysteine, L-aspartic acid and L-glutamic acid. This specially blended amino acid protein source provides renal patients with an optimal essential to non-essential amino acid ratio of approximately 2:1 to 4:1. As a result, the high quality protein source enables patients to maintain proper nitrogen balance without excessive protein intake.

In an embodiment, the composition has a caloric density ranging from 1.6 to 2.25 kcal/ml.

In another embodiment, the composition is only supplemented with water soluble vitamins. The composition is essentially free of fat soluble vitamins to avoid the possible toxic effects of same.

Likewise, in an embodiment, the composition is essentially free of electrolytes.

The present invention also provides a method for treating and preventing renal failure. The method includes the step of enterally administering to a patient having renal failure or at risk of same a nutritional composition. The nutritional composition includes free amino acids supplemented with a portion of whey protein. The composition uniquely has a caloric density ranging from approximately 1.6 to 2.25 kcal/ml.

In an embodiment, the composition comprises a mixture of medium and long-chain triglycerides having a ratio of approximately 1:1 to 4:1.

Still further, the present invention further provides a method for treating renal failure comprising the step of enterally administering to a patient having renal failure or at risk of same a composition comprising a protein source and a lipid source. The protein source includes whey protein and free amino acids that together provide the needed essential and non-essential amino acids. The lipid source includes medium-chain triglycerides and preferably provides approximately 18% to 28% of the total caloric content of the composition.

An advantage of present invention is that it provides an improved nutritional composition for the treatment of acute or chronic renal patients requiring a balanced, low protein diet.

Another advantage of the present invention is that it has a very high caloric density, thereby providing patients sufficient energy with restricted water intake. Moreover, the product promotes ease of adjusting daily fluid needs.

Still further, an advantage of the present invention is that it is provided in a shelf-stable, ready-to-use liquid form. As a result, the composition is convenient and reduces the risk of contamination during preparation.

Yet another advantage of the present invention is that it provides an amino acid based, liquid ready-to-use product with a moderate osmolality. The moderate osmolality provides a composition that can be easily tolerated by patients.

Moreover, an advantage of the present invention is that it provides a composition that is virtually electrolyte-free, thereby promoting ease of tailoring daily electrolyte needs.

Still further, an advantage of the present invention is that it includes a source of medium-chain triglycerides. Medium-chain triglycerides can satisfy the patient's high caloric requirements without creating fat intolerant conditions.

Another advantage of the present invention is that it is only supplemented with selected minerals that are beneficial to the patient's conditions.

Moreover, another advantage of the present invention is that it is only supplemented with water soluble vitamins.

Additional features and advantages of the present invention are described in, and will be apparent from, the detailed description of the presently preferred embodiments.

DETAILED DESCRIPTION OF THE PRESENTLY PREFERRED EMBODIMENTS

The kidneys play a critical role in maintaining the body's physiologic milieu. The kidneys excrete, secrete, synthesize, regulate, and degrade metabolic substances as well as participate in the metabolism of hormones. When these functions deteriorate as a result of renal failure, various metabolic abnormalities occur that impinge on nutritional status. Moreover, as renal failure progresses, accumulation of toxic substances further affects the body's nutritional and metabolic states, causing an increased requirement for nutrients.

Nutritional support of patients requires prevention, recognition and treatment of nutritional depletion that may occur with illness, such as renal failure. The goals of nutritional support include stabilizing metabolic state, maintaining body mass, and/or facilitating growth in the presence of disease. With respect to renal failure, the role of nutritional support is to prevent or reverse associated malnourished states, minimize the adverse effects of nutrients and metabolites that are inadequately excreted, and favorably affect the progression and outcome of renal failure.

The present invention provides a product that is specifically directed to meet the needs of patients suffering from renal failure. To this end, the present invention provides an amino acid based, liquid ready-to-use product having a very high caloric density with a moderate osmolality.

The composition of the present invention provides a unique protein source that is specifically designed for renal patients. Due to a variety of factors, uremic patients suffering from renal failure are often in a negative nitrogen balance and tend to lose muscle mass. In order to counteract such conditions, the present invention incorporates a specially blended amino acid profile containing free amino acids and whey protein.

The composition preferably provides an optimal essential amino acid to non-essential amino acid ratio ranging from approximately 2:1 to 4:1. In an embodiment, the essential to non-essential amino acid ratio is approximately 2:1. In an embodiment, the essential amino acids provide 23.0 g/l and the nonessential amino acids provide 11.4 g/l of the composition. The resulting high quality protein source enhances nitrogen utilization in the uremic patient by providing the needed precursors for protein synthesis in proportions that minimize excessive formation of urea.

The composition of the present invention is an amino acid based diet. The composition consists of free amino acids and whey protein. As one skilled in the art will appreciate, the whey protein can be in a variety of forms without departing from the scope of the present invention. For example, the whey protein can be an intact protein and/or hydrolyzed protein (i.e. peptides produced by a protein degradation).

The specific amino acid profile of the present invention provides the key advantages outlined above for the treatment of renal failure patients. Pursuant to the present invention, the amino acid profile preferably contains the following amino acids in the approximate recited mole percent ranges.

| Amino Acid | Mole Percent Ranges |
| --- | --- |
| L-Valine | 12.3 to 14.8 |
| L-Leucine | 8.0 to 9.7 |
| L-Isoleucine | 6.8 to 8.2 |
| L-Threonine | 5.7 to 6.9 |
| L-Methionine | 6.5 to 7.9 |
| L-Lysine | 5.5 to 6.6 |
| L-Phenylalanine | 5.3 to 6.4 |
| L-Tryptophan | 1.4 to 1.6 |
| L-Histidine | 6.3 to 7.6 |
| L-Arginine | 6.1 to 7.4 |
| L-Proline | 3.9 to 4.8 |
| Glycine | 7.1 to 8.6 |
| L-Alanine | 6.1 to 7.4 |
| L-Serine | 3.0 to 3.7 |
| L-Tyrosine | 0.5 to 0.8 |
| L-Cysteine | 0.6 to 1.1 |
| L-Aspartic Acid | 2.0 to 3.4 |
| L-Glutamic Acid | 2.7 to 4.7 |

The protein source of the present invention preferably provides approximately 5 to 10% of the total calories of the composition. In an embodiment, the protein source comprises approximately 6.9% of the total calories of the composition. This amount coupled with the ratio of essential to non-essential amino acids provided in the present invention helps maintain a positive nitrogen balance with low protein intake, while contributing to the control of uremia.

Carbohydrates provide, in an embodiment, approximately 50% to 65% of the total caloric content of the composition. In a preferred embodiment, the carbohydrate source is approximately 58.1% of the total caloric content of the composition. A number of carbohydrates can be used, pursuant to the present invention, including maltodextrin and hydrolyzed corn starch.

The lipid source of the present invention includes a mixture of medium-chain triglycerides (MCT) and long-chain triglycerides (LCT). The lipid source of the present invention is approximately 25% to about 40% of the caloric content of the composition. In a preferred embodiment, the lipid source is approximately 35% of the caloric content of the composition. This amount coupled with the use of MCTs provides a calorically-dense energy source that allows for better fat absorption.

The lipid profile of the present invention is designed to meet essential fatty acid needs (omega-3 and omega-6) while also keeping MCT content high and LCT content low compared with prior formulas. In an embodiment, the lipid source of the present invention includes at least 70% from medium-chain triglycerides. In a preferred embodiment, the medium-chain triglyceride source is fractionated coconut oil.

The use of MCTs in the lipid source provides a variety of benefits over prior formulations. For instance, the inclusion of MCT oil ensures that the diet may be used in patients with concomitant malabsorption syndromes, which often occurs in patients with renal failure. Such medium-chain triglycerides are easily absorbed and metabolized in the renal patient. Moreover, the preferred 70:30 ratio of the present invention sufficiently satisfies patients' high caloric requirements without creating fat intolerant conditions. The composition provides a more calorically dense energy source as compared with products comprised of only long-chain triglycerides.

The remainder of the lipid source is a mixture of long-chain triglycerides. Suitable sources of long-chain triglycerides are canola oil, corn oil, soy lecithin and residual milk fat. The lipid profiles containing such long-chain triglycerides are designed to have a polyunsaturated fatty acid omega-6 (n-6) to omega-3 (n-3) ratio of approximately 1:1 to 10:1. In an embodiment, the composition includes an omega-6 to omega-3 ratio of 4:1.

In addition to the requirements for protein, carbohydrate and lipid, renal patients also have elevated requirements of certain vitamins, minerals and trace elements. The present invention includes a specialized vitamin profile. However, the electrolytes and minerals are excluded or minimized to allow flexibility in the adding of minerals/electrolytes for the prescribing caretaker.

Preferably, the present invention provides 100% of the U.S. RDA of vitamins in 2000 kcal. In an embodiment, composition includes only water-soluble vitamins. Water-soluble vitamins, which are lost in dialysis, are often deficient in uremic patients. Fat soluble vitamins, which are not lost during dialysis and can accumulate to toxic levels, are excluded from the composition to avoid the possible toxic effects of same.

Certain key vitamins are added at increased levels in order to meet the specific needs of the renal patient. For example, hyperphophatemia can inhibit folate uptake in the cell. As a result, the composition of the present invention preferably includes at least 150% of the U.S. RDA of folic acid. Likewise, pyridoxine metabolism is altered in uremia, and deficiencies are likely to develop. Thus, the composition of the present invention preferably includes at least 350% of the U.S. RDA of vitamin $B_6$.

With respect to the supplemented select minerals, only those minerals that are beneficial to the patients' conditions are added. In this regard, zinc as well as selenium are supplemented to prevent possible deficiencies of same. In an embodiment, 10 to 30 mg per 2000 calories of zinc is provided; whereas, 40 to 120 mcg per 2000 calories of selenium is provided. In a preferred embodiment, 14 mg of zinc and 50 mcg of selenium is provided in the composition.

As noted above, the composition is preferably free of electrolytes. Patients with renal failure are unable to excrete electrolytes normally. Thus, through carefully selected ingredients, use of demineralized maltodextrin and electrolyte-free amino acids, the formula is virtually electrolyte free. As a result, the product of the present invention minimizes accumulation of electrolytes in the blood and permits a clinician controlled intake of these nutrients. Patients have maximum flexibility in customizing their diet according to their electrolyte requirements.

The composition of the present invention is a ready-to-use enteral formulation. Unlike many prior formulations, the present invention provides a convenient and easy to use product. Providing the composition in liquid form results in decreased risk of contamination as well as less waste as compared to prior powder formulas.

The composition can be used as a supplement or for total enteral nutritional support. The composition can be tube-fed to a patient, or fed by having the patient drink same. Uniquely, the composition of the present invention has a moderate osmolality, facilitating easy tolerance for renal patients. In an embodiment, the composition has an osmolality of approximately 400 to 800 mOsm/kg. In a preferred embodiment, osmolality of the composition is approximately 600 mOsm/kg.

Many renal patients have increased energy needs while at the same time are fluid restricted. Therefore, providing high caloric intake to patients is critical for treating renal failure. To this end, the present invention not only provides a ready-to-use product but also provides a product that is calorically dense. In an embodiment, the composition has a caloric density of approximately 1.6 kcal/ml to approximately 2.25 kcal/ml. Preferably, the caloric density of the composition is 2.0 kcal/ml. The composition thereby provides patients sufficient energy with restricted water intake.

The composition of the present invention is preferably utilized to treat or prevent renal failure. Typically, on average, approximately 2000 kcal of the composition will be given per day to a renal patient. Of course, some patients with very high requirements will require substantially more composition and some patients with lower requirements, and/or weights, may require less composition. As one skilled in the art will recognize, the administration of the composition may be varied to refine the responsiveness of the renal failure patient in the particular clinical circumstances at hand. For instance, key factors that affect the amount of composition to be administered include the progress and extent of renal failure, the presence of complications or the disease states, and whether or not dialysis is concurrent. These factors and the degree of dietary protein restriction, if any, are balanced to arrive at optimal maintenance.

The effectiveness of the dietary program may be monitored by well known assays for assessing renal function in dialyzed or non-dialyzed patients as appropriate. Suitable examples include serum urea nitrogen (SUN), SUN/creatinine ratio, urea nitrogen appearance and glomerular filtration rate for creatinine. Other diagnostic mechanisms will be apparent to the ordinary person skilled in the art.

By way of example, and not limitation, an example of a suitable composition that may be used pursuant to the present invention is as follows.

The composition includes the following ingredients: water; maltodextrin, medium-chain triglycerides, (MCT source: fractionated coconut oil); canola oil; whey protein concentrate; modified corn starch, L-valine; corn oil; L-arginine, L-histidine, L-methionine, L-phenylalanine; L-leucine; L-lysine acetate; L-isoleucine; soy lecithin, glycine; L-threonine L-alanine; L-proline; choline bitartrate; L-tryptophan; L-serine; ascorbic acid; L-carnitine; taurine; zinc sulfate; niacinamide; calcium pantothenate; pyridoxine hydrochloride; biotin; riboflavin; thiamine mononitrate; folic acid; sodium selenate and cyanocobalamin.

The composition of the present invention has the following nutrient composition (per 500 kcal):

| Nutrient Composition | Amount | % U.S. RDA* |
|---|---|---|
| Protein | 8.6 g | 19 |
| Carbohydrate | 72.6 g | ** |
| Fat*** | 20.6 g | ** |
| Water | 176 ml | ** |
| Vitamin C | 15 mg | 25 |
| Vitamin $B_1$ | .38 mg | 25 |
| Vitamin $B_2$ | .43 mg | 25 |
| Niacin | 5 mg | 25 |
| Vitamin $B_6$ | 1.75 mg | 88 |
| Folic Acid | 150 mcg | 38 |
| Pantoth. Acid | 2.5 mg | 25 |
| Vitamin $B_{12}$ | 1.5 mcg | 25 |
| Biotin | 75 mcg | 25 |
| Choline | 100 mg | ** |
| Taurine | 25 mg | ** |
| L-Carnitine | 25 mg | ** |
| Zinc | 3.5 mg | 23 |
| Selenium | 12.5 mcg | ** |

Legend
*U.S. Recommended Daily Allowance for Adults and Children 4 or More Years of Age
**U.S. RDA Not Established
***MCT Provides 14.4 grams Per 500 Kcal It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An enteral composition for providing nutrition to a patient suffering from or at risk of renal failure comprising:

a therapeutically effective amount of a protein source including free amino acids and whey protein, the protein source having an essential amino acid to non-essential amino acid ratio of approximately 2:1 to 4:1 and an amino acid profile comprising L-valine, L-leucine, L-isoleucine, L-threonine, L-methionine, L-lysine, L-phenylalanine, L-tryptophan, L-histidine, L-arginine, L-proline, glycine, L-alanine, L-serine, L-tyrosine, L-cysteine, L-aspartic acid and L-glutamic acid, and the composition having a caloric density ranging from approximately 1.6 kcal/ml to 2.25 kcal/ml.

2. The composition of claim 1 further comprising a mixture of medium and long-chain triglycerides having a ratio of approximately 1:1 to 4:1.

3. The composition of claim 1 further comprising water soluble vitamins.

4. The composition of claim 1 which is essentially free of electrolytes and fat soluble vitamins.

5. The composition of claim 1 in which the protein source has the following amino acid profile:

| Amino Acid | Mole Percent Ranges |
|---|---|
| L-Valine | 12.3 to 14.8 |
| L Leucine | 8.0 to 9.7 |
| L-Isoleucine | 6.8 to 8.2 |
| L-Threonine | 5.7 to 6.9 |
| L-Methionine | 6.5 to 7.9 |
| L-Lysine | 5.5 to 6.6 |
| L-Phenylalanine | 5.3 to 6.4 |
| L-Tryptophan | 1.4 to 1.6 |
| L-Histidine | 6.3 to 7.6 |
| L-Arginine | 6.1 to 7.4 |
| L- Proline | 3.9 to 4.8 |
| Glycine | 7.1 to 8.6 |
| L-Alanine | 6.1 to 7.4 |
| L-Serine | 3.0 to 3.7 |
| L-Tyrosine | 0.5 to 0.8 |
| L-Cysteine | 0.6 to 1.1 |
| L-Aspartic Acid | 2.0 to 3.4 |
| L-Glutamic Acid | 2.7 to 4.7 |

6. A method for providing nutrition to a patient suffering from or at risk of renal failure comprising the step of enterally administering to the patient a composition comprising a therapeutically effective amount of a protein source including whey protein and free amino acids and having an essential to non-essential amino acid ratio of approximately 2:1 to 4:1, the composition having a caloric density ranging from approximately 1.6 kca/ml to 2.25 kcal/ml.

7. The method of claim 6 further comprising a mixture of medium and long-chain triglycerides having a ratio of approximately 1:1 to 4:1.

8. The method of claim 6 further comprising water soluble vitamins.

9. The method of claim 6 which is essentially free of electrolytes and fat soluble vitamins.

10. The method of claim 6 wherein the protein source has an amino acid profile comprising L-valine, L-leucine, L-isoleucine, L-threonine, L-methionine, L-lysine, L-phenylalanine, L-tryptophan, L-histidine, L-arginine, L-proline, glycine, L-alanine, L-serine, L-tyrosine, L-cysteine, L-aspartic acid and L-glutamic acid.

11. The method of claim 10 in which the protein source has the following amino acid profile:

| Amino Acid | Mole Percent Ranges |
|---|---|
| L-Valine | 12.3 to 14.8 |
| L-Leucine | 8.0 to 9.7 |
| L-Isoleucine | 6.8 to 8.2 |
| L-Threonine | 5.7 to 6.9 |
| L-Methionine | 6.5 to 7.9 |
| L-Lysine | 5.5 to 6.6 |
| L-Phenylalanine | 5.3 to 6.4 |
| L-Tryptophan | 1.4 to 1.6 |
| L-Histidine | 6.3 to 7.6 |
| L-Arginine | 6.1 to 7.4 |
| L-Proline | 3.9 to 4.8 |
| Glycine | 7.1 to 8.6 |
| L-Alanine | 6.1 to 7.4 |
| L-Serine | 3.0 to 3.7 |
| L-Tyrosine | 0.5 to 0.8 |
| L-Cysteine | 0.6 to 1.1 |
| L-Aspartic Acid | 2.0 to 3.4 |
| L-Glutamic Acid | 2.7 to 4.7 |

12. A method for providing nutrition to a patient suffering from or at risk of renal failure comprising the step of enterally administering to the patient a composition comprising:

a protein source including whey protein and free amino acids; and a lipid source containing medium chain triglycerides and comprising 18% to 28% of the total caloric content of the composition.

13. The method of claim 12 wherein the whey protein comprises from approximately 0% to 50% of the protein source.

14. The method of claim 12 wherein the free amino acids comprise from approximately 50% to 100% of the protein source.

15. The method of claim 12 wherein the lipid source comprises long-chain triglycerides, the medium to long-chain triglycerides ratio being approximately 1:1 to 4:1.

16. The method of claim 12 wherein the composition has an essential amino acid to nonessential amino acid ratio of approximately 2:1 to 4:1.

17. The method of claim 12 further comprising water soluble vitamins.

18. The method of claim 12 which is essentially free of electrolytes and fat soluble vitamins.

19. The method of claim 12 wherein the protein source has an amino acid profile comprising L-valine, L-leucine, L-isoleucine, L-threonine, L-methionine, L-lysine, L-phenylalanine, L-tryptophan, L-histidine, L-arginine, L-proline, glycine, L-alanine, L-serine, L-tyrosine, L-cysteine, L-aspartic acid and L-glutamic acid.

20. The method of claim 19 in which the protein source has the following amino acid profile:

| Amino Acid | Mole Percent Ranges |
| --- | --- |
| L-Valine | 12.3 to 14.8 |
| L-Leucine | 8.0 to 9.7 |
| L-Isoleucine | 6.8 to 8.2 |
| L-Threonine | 5.7 to 6.9 |
| L-Methionine | 6.5 to 7.9 |
| L-Lysine | 5.5 to 6.6 |
| L-Phenylalanine | 5.3 to 6.4 |
| L-Tryptophan | 1.4 to 1.6 |
| L-Histidine | 6.3 to 7.6 |
| L-Arginine | 6.1 to 7.4 |
| L-Proline | 3.9 to 4.8 |
| Glycine | 7.1 to 8.6 |
| L-Alanine | 6.1 to 7.4 |
| L-Serine | 3.0 to 3.7 |
| L-Tyrosine | 0.5 to 0.8 |
| L-Cysteine | 0.6 to 1.1 |
| L-Aspartic Acid | 2.0 to 3.4 |
| L-Glutamic Acid | 2.7 to 4.7 |

21. An enteral composition for providing nutrition to a patient suffering from or at risk of renal failure comprising:
a therapeutically effective amount of a protein source including free amino acids and whey protein, the protein source having an amino acid profile as follows:

| Amino Acid | Mole Percent Ranges |
| --- | --- |
| L-Valine | 12.3 to 14.8 |
| L-Leucine | 8.0 to 9.7 |
| L-Isoleucine | 6.8 to 8.2 |
| L-Threonine | 5.7 to 6.9 |
| L-Methionine | 6.5 to 7.9 |
| L-Lysine | 5.5 to 6.6 |
| L-Phenylalanine | 5.3 to 6.4 |
| L-Tryptophan | 1.4 to 1.6 |
| L-Histidine | 6.3 to 7.6 |
| L-Arginine | 6.1 to 7.4 |
| L-Proline | 3.9 to 4.8 |
| Glycine | 7.1 to 8.6 |
| L-Alanine | 6.1 to 7.4 |
| L-Serine | 3.0 to 3.7 |
| L-Tyrosine | 0.5 to 0.8 |
| L-Cysteine | 0.6 to 1.1 |
| L-Aspartic Acid | 2.0 to 3.4 |
| L-Glutamic Acid | 2.7 to 4.7 |

22. The composition of claim 21 having a caloric density ranging from approximately 1.6 kcal/ml to 2.25 kcal/ml.

23. The composition of claim 21 further comprising a mixture of medium and long-chain triglycerides having a ratio of approximately 1:1 to 4:1.

* * * * *